United States Patent [19]

Bonifaz et al.

[11] Patent Number: 4,613,720
[45] Date of Patent: Sep. 23, 1986

[54] BORON-TREATED ZEOLITE CATALYST FOR PREPARING LIGHT MONOOLEFINS

[75] Inventors: Cristobal Bonifaz, Greenville, Del.; David R. Corbin, West Chester, Pa.; John B. Parise, New South Wales, Australia

[73] Assignee: E. I. Du Pont de Nemours and Company, Wilmington, Del.

[21] Appl. No.: 818,806

[22] Filed: Jan. 14, 1986

[51] Int. Cl.$^4$ .............................................. C07C 1/20
[52] U.S. Cl. ..................................... 585/640; 502/63; 502/64; 585/469; 585/408; 585/733
[58] Field of Search ............... 585/640, 639, 638, 469, 585/408; 502/63, 64

[56] References Cited

U.S. PATENT DOCUMENTS

| | | | |
|---|---|---|---|
| 3,644,220 | 2/1972 | Kearby | 502/73 |
| 3,911,041 | 10/1975 | Kaeding et al. | 585/711 |
| 4,049,573 | 9/1977 | Kaeding | 502/77 |
| 4,062,905 | 12/1977 | Chang et al. | 585/640 |
| 4,079,095 | 3/1978 | Givens et al. | 585/640 |
| 4,079,096 | 3/1978 | Givens et al. | 585/640 |
| 4,115,424 | 9/1978 | Unland et al. | 502/79 |
| 4,140,726 | 2/1979 | Unland et al. | 585/438 |
| 4,192,770 | 3/1980 | Singleton | 502/31 |
| 4,229,608 | 10/1980 | Chen et al. | 585/640 |
| 4,230,894 | 10/1980 | Young | 568/768 |
| 4,247,731 | 1/1981 | Wunder et al. | 585/640 |
| 4,254,297 | 3/1981 | Frenken et al. | 585/640 |
| 4,264,473 | 4/1981 | Tu et al. | 502/64 |
| 4,296,266 | 10/1981 | Wunder et al. | 585/640 |
| 4,300,012 | 11/1981 | Tu et al. | 585/470 |
| 4,393,265 | 7/1983 | Bonifaz | 585/639 |
| 4,423,272 | 12/1983 | Forbus et al. | 585/640 |
| 4,481,376 | 11/1984 | Wunder et al. | 585/640 |

FOREIGN PATENT DOCUMENTS

| | | |
|---|---|---|
| 0011900 | 11/1980 | European Pat. Off. . |
| 0063436 | 10/1982 | European Pat. Off. . |
| 0074075 | 3/1983 | European Pat. Off. . |
| 0075203 | 3/1983 | European Pat. Off. . |
| 0090283 | 5/1983 | European Pat. Off. . |

OTHER PUBLICATIONS

Singh et al., *Chem. Eng. Commun.*, 4:749–758 (1980).
Kaeding et al., *J. Catalysis*, 61:155–164 (1980).
Chang et al., *J. Catalysis*, 86, 289–296 (1984).
Chu et al., *J. Catalysis*, 86, 297–300 (1984).
Keading et al., *J. Catalysis*, 67:159–174 (1981).
Kaeding et al., *J. Catalysis*, 69, 392–398 (1981).

*Primary Examiner*—Andrew H. Metz
*Assistant Examiner*—A. Pal

[57] ABSTRACT

A process for preparing light monoolefins, particularly ethylene and propylene, from a feed stream comprising a reactant consisting of methanol, dimethyl ether or mixtures thereof in the presence of a boron-treated aluminosilicate zeolite catalyst is disclosed.

7 Claims, No Drawings

BORON-TREATED ZEOLITE CATALYST FOR PREPARING LIGHT MONOOLEFINS

BACKGROUND OF THE INVENTION

1. Field of the Invention

This invention relates to a process and catalyst for preparing light monoolefins, particularly ethylene and propylene, from a feed stream comprising a reactant consisting of methanol, dimethyl ether, or mixtures thereof.

2. Background of the Art

The following references disclose methods for preparing monoolefins containing 2 to 4 carbon atoms from methanol and/or dimethyl ether in the presence of both natural and synthetic zeolitic catalysts. U.S. Pat. No. 4,062,905, issued to Chang et al., discloses a process for converting a charge consisting essentially of methanol, dimethyl ether, or mixtures thereof to a hydrocarbon product rich in ethylene and propylene with a catalyst comprising a crystalline aluminosilicate zeolite having pores which are less than 6 Angstroms (0.6 nm) in the major dimension. Operable catalysts include chabazite, erionite, zeolite T and zeolite ZK-5, preferably in the hydrogen form. Reaction conditions include an operating temperature of about 500° F. (260° C.) to about 1100° F. (593° C.), a pressure of about 0.2 to about 30 atmospheres (about 20 to about 3000 kPa), and a liquid hourly space velocity of about 0.1 to about 200. Also disclosed is the use of carrier gases or diluents, for example, helium, hydrogen or nitrogen. Patentees exemplify yields of 44 wt % ethylene and 33 wt % propylene at 5% conversion, and 46 wt % ethylene and 26 wt % propylene at 80% conversion. The catalyst is regenerated (de-carbonized) by heating in air.

U.S. Pat. No. 4,079,095, issued to Givens et al., discloses a process for converting an organic charge consisting essentially of methanol, dimethyl ether or mixtures thereof together with at least about 0.25 moles of water per mole of the organic charge to a hydrocarbon product rich in ethylene and propylene with a catalyst comprising a crystalline aluminosilicate zeolite of the erionite-offretite type. Reaction conditions include an operating temperature of about 500° F. (260° C.) to about 1000° F. (538° C.), a pressure of about 0.2 to about 30 atmospheres (about 20 to about 3000 kPa), and a weight hourly space velocity of about 0.1 to about 30 h$^{-1}$. The zeolite catalyst is preferably employed in its hydrogen form and can be regenerated by heating in air. The related U.S. Pat. No. 4,079,096, also issued to Givens et al., discloses a similar process using ZSM-34, a crystalline aluminosilicate zeolite of the erionite-offretite type, as the catalyst.

U.S. Pat. No. 4,247,731, issued to Wunder et al., discloses the production of lower alkenes, especially ethylene, from methanol and/or dimethyl ether in the presence of aluminum silicate catalysts containing manganese and possibly further co-catalysts. Suitable aluminum silicate catalysts include faujasites, zeolites, chabazites, analcites, gismondites, gmelinites, natrolites, erionites and mordenites, which contains 0.1 to 10 wt% manganese and, optionally, another metal, for example, magnesium, as a co-catalyst. The manganese can be applied to the aluminum silicate by impregnation with a solution of manganese salt. Reaction conditions include a temperature in the range of from 300° to 500° C., preferably 350° to 450° C., and more preferably 380° to 420° C. The catalyst is regenerated under relatively mild conditions by burning off coke deposits with air or oxygen and steam. A hydrocarbon product containing 46.9% ethylene and 29.2% propylene is exemplified.

U.S. Pat. No. 4,229,608, issued to Chen et al., discloses a cyclic process for converting a charge consisting essentially of methanol, dimethyl ether or mixtures thereof to a hydrocarbon product rich in ethylene and propylene with a catalyst comprising a crystalline aluminosilicate zeolite having pores which are less than 6 Angstroms (0.6 nm) in the major dimension. Suitable zeolites include chabazite, erionite, zeolite T and zeolite ZK-5. Reaction conditions include a temperature of about 800° to about 1150° F. (about 430° to about 620° C.), and a residence time of less than 30 seconds, preferably less than 15 seconds. The catalyst is separately regenerated in air at 1200° to 1400° F. (650° to 760° C.).

Singh et al., Chem. Eng. Commun., 4:749–758 (1980) discloses the conversion of methanol to olefins with a chabazite zeolite ion-exchanged with ammonium hydroxide and a rare earth chloride mixture. Catalyst life may be extended if carbon disulfide is present in the feed stream. The addition of water to the feed enhances selectivity towards olefins and a yield of ethylene of over 60 wt % is reported when a mixture of 36% methanol, 64% water and 2000 ppm of carbon disulfide is passed over the catalyst.

U.S. Pat. No. 3,911,041, issued to Kaeding et al., and Kaeding et al., J. Catalysis, 61:155–164 (1980) disclose the conversion of methanol to water and hydrocarbons, with up to 70% selectivity to $C_2$–$C_4$ olefins at 100% conversion over a crystalline aluminosilicate zeolite having a silica to alumina ratio of at least about 12, a constraint index of about 1 to 12, and having at least about 0.78 weight percent phosphorus incorporated with the crystal structure. Suitable zeolites include ZSM-5, ZSM-11, ZSM-12, ZSM-21, and TEA-mordenite.

Chang et al., J. Catalysis, 86, 289–296 (1984) and Chu et al., J. Catalysis, 86, 297–300 (1984), report on a study of the conversion of methanol to olefins over the zeolite ZSM-5. Selectivity to olefins can be enhanced by increasing the temperature of reaction and increasing the $SiO_2/Al_2O_3$ ratio of the zeolite catalyst.

U.S. Pat. No. 4,393,265, issued to Bonifaz, discloses a process for preparing hydrocarbons rich in light monoolefins by contacting a feed stream consisting essentially of dimethyl ether or a mixture of methanol and dimethyl ether with hydrogen-exchanged aluminosilicate catalyst having a silica to alumina ratio of less than 12 and, optionally, containing added metal cations. The catalyst is activated by treating with steam at a temperature of at least 400° C., preferably 450° to 520° C. The feed stream contains sufficient water such that the mole ratio of water to ether in the reaction zone is at least 0.3. At least 85 wt % of the reactant is converted to hydrocarbons comprising at least 50 wt % ethylene and propylene, said 85% conversion being achieved before the contacting has exceeded 1 g of reactant per g of catalyst. Spent catalyst is regenerated by treating with a mixture comprising steam and oxygen at a temperature of at least 400° C., preferably 450° to 520° C.

U.S. Pat. No. 4,296,266, issued to Wunder et al., discloses a process for converting methanol and/or dimethyl ether to $C_2$–$C_4$ olefins in the presence of water and a manganese-containing aluminum silicate catalyst. Before or after application of the manganese, the aluminum silicate is washed with a solution of ethylenediaminetetraacetic acid or tartaric acid adjusted to a pH of 3 to 7 by means of a base.

U.S. Pat. No. 4,049,573, issued to Kaeding, discloses a catalytic process for converting lower monohydric alcohols and their ethers, especially methanol and dimethyl ether to a hydrocarbon mixture rich in $C_2$–$C_3$ olefins and mononuclear aromatics with high selectivity for para-xylene production with a catalyst comprising a crystalline aluminosilicate zeolite having a silica to alumina ratio of at least about 12 and a constraint index of about 1 to 12. The catalyst contains at least about 0.25 weight percent of an oxide of boron or magnesium, either alone or in combination or in further combination with an oxide of phosphorus. Suitable zeolites include ZSM-5, ZSM-11, ZSM-12, ZSM-35 and ZSM-38. By operating at lower reaction temperatures, the process can be made to produce primarily light olefins. The proportions of olefins and aromatic hydrocarbons that are produced may also be varied by varying the ratio of metal oxide to crystalline aluminosilicate, higher metal oxide contents favoring olefin formation.

European Patent Application No. 0 011 900 discloses a process for the conversion of dimethyl ether into a mixture of substantially aliphatic hydrocarbons, substantially propylene and butylenes, and water using a catalyst that consists of a crystalline modification of silica in which some silicon atoms are replaced by a crystalline modification of boron atoms. The amount of boron in the crystalline modification expressed as the molar ratio of oxides $B_2O_3$ and $SiO_2$ may vary between 0.0005 and 0.025, but larger amounts can be used. The modified silica is prepared by heating pure silica dissolved in a tetra alkylammonium hydroxide with a solution of a boron compound such as boric acid, sodium borate, ammonium borate, soluble perborates and pyroborates, and soluble organic compounds. The resulting crystalline product is washed, dried and calcined.

European Patent Application No. 0 090 283 discloses a process for the conversion of methanol and/or dimethyl ether to olefins using a borosilicate zeolite as the catalyst to obtain an improved $C_2$–$C_4$ olefin yield. European Patent Application 0 074 075 discloses a process for the conversion of methanol and/or dimethyl ether to low-molecular-weight olefins using a borosilicate zeolite as the catalyst and a two-step process in which, for example, after the first step, the $C_2$–$C_4$ olefins or just ethylene and propylene are separated and the remaining hydrocarbons sent on to a second reaction step. European Patent Application No. 0 075 203 discloses a process for the conversion of methanol and/or dimethyl ether to obtain high yields of $C_2$–$C_4$ olefins using a borosilicate zeolite as the catalyst with the reaction undertaken with the addition of small amounts of electron donors such as substituted hydrocarbons, organic acids and amines, substituted silanes, certain silicon-containing compounds, and certain sulfur, phosphorus, arsenic and antimony compounds.

European Patent Application No. 0 063 436 discloses a synthetic zeolite material, designated zeolite EU-4 having oxides of one or more of aluminum, iron, chromium, vanadium, molybdenum, arsenic, antimony, manganese, gallium or boron. A process for the conversion of methanol to $C_1$–$C_4$ hydrocarbons rich in olefins using synthetic zeolite EU-4 is also disclosed.

The following references disclose zeolites which have been treated with a boron compound to improve selectivity in a catalytic reaction. U.S. Pat. No. 4,264,473 and U.S. Pat. No. 4,300,012, both issued to Tu et al., disclose a catalytic composite effective with respect to the transalkylation of alkylaromatic hydrocarbons particularly toluene. The composite catalyst is prepared by subjecting a mordenite alumina to an aqueous ammoniacal treatment at a pH of at least about 9.5, calcining the resulting mordenite alumina, subjecting the calcined mordenite alumina to an aqueous solution containing a boron salt, and calcining the resulting mordenite alumina.

U.S. Pat. No. 4,115,424 and U.S. Pat. No. 4,140,726, both issued to Unland et al., disclose an improved alkylation catalyst for producing styrene and ethylbenzene from toluene and methanol. The catalyst is a faujasite type zeolite with cesium, rubidium or potassium cations, and containing boron or phosphorus.

U.S. Pat. No. 4,192,770, issued to Singleton, discloses a process for restoring selectivity of zeolite-containing cracking catalyst which are contaminated with nickel, vanadium, and/or iron during cracking operations. The process comprises contacting the catalyst with a boron compound for a time sufficient to apply less than 1 weight percent boron to the cracking catalyst.

Kaeding et al., *J. Catalysis,* 67:159–174 (1981) discloses selective alkylation of toluene with methanol over ZSM-5 class zeolite catalysts to produce xylenes and water. Over 90% para isomer in the xylene product was achieved when the catalyst was modified by impregnation with phosphorus compounds and with boron compounds. The acid or ammonium form of the zeolite was treated with solutions of various phosphorus or boron compounds, dried, and calcined. A steady increase in selectivity to the para isomer was observed with time; this is a general phenomenon associated with coke deposition on the catalyst. Kaeding et al., *J. Catalysis,* 69, 392–398 (1981) discloses selective disproportionation of toluene to produce benzene and xylenes rich in the para isomer over ZSM-5 zeolites which were modified with phosphorus, boron, or magnesium compounds as described in the previous Kaeding et al. reference.

U.S. Pat. No. 4,230,894, issued to Young, discloses a process for producing hydroxybenzene compounds having substituents in the 1 and 3 positions on the benzene ring, from an isomeric mixtures of dialkylbenzene compounds over a crystalline aluminosilicate zeolite having a silica to alumina ratio of at least about 12, a constraint index of about 1 to 12, and having undergone prior modification by combining therewith between about 0.25 and about 40 percent by weight of at least one oxide selected from the group consisting of the oxides of phosphorus, antimony, boron, and magnesium. Suitable zeolites include ZSM-5, ZSM-11, ZSM-12, ZSM-35 and ZSM-38. Modification of the zeolite with the desired oxide can readily be accomplished by contacting the zeolite with a solution of an appropriate compound of the element to be introduced, followed by drying and calcining to convert the compound to its oxide form. The compound of the element can be in the gaseous phase.

U.S. Pat. No. 3,644,220, issued to Kearby, discloses novel metal halide containing zeolites. The zeolites are prepared by reacting alkali or alkaline earth or hydrogen forms of crystalline aluminosilicate zeolites with volatile halides of metals and non-metals. Volatile halides of metal elements such as aluminum, zirconium, titanium, tin, molybdenum, tungsten, chromium, vanadium, antimony, bismuth, iron, platinum, palladium and the rare earths are described. Halides of non-metals such as arsenic, silica, boron, or phosphorus are also disclosed.

None of these references discloses the use of a boron-treated zeolite of the instant invention as the catalyst for preparing light monoolefins, particularly ethylene and propylene, from a gas stream comprising methanol, dimethyl ether or a mixture thereof.

SUMMARY OF THE INVENTION

The present invention provides a catalyst and process for preparing light monoolefins from a feed stream comprising a reactant consisting of methanol, dimethyl ether, or a mixture thereof. The process comprises contacting the feed stream at a weight hourly space velocity of greater than about 0.5 $h^{-1}$ with an aluminosilicate zeolite catalyst at a temperature of from about 350° to about 600° C. and a pressure of from about 20 to about 3000 kPa. The process converts at least about 85 weight percent of the reactant to hydrocarbons comprising at least 60 weight percent ethylene and propylene, said 85 weight percent conversion being achieved before the contacting has exceeded 0.3 gram of reactant per gram of catalyst. The aluminosilicate zeolite catalyst comprises an aluminosilicate zeolite having a silica to alumina ratio of less than about 12. The aluminosilicate zeolite catalyst is prepared by depositing a boron containing species on the surface region of the aluminosilicate zeolite. The aluminosilicate zeolite catalyst has a boron to aluminum atom ratio in the surface region of the catalyst of less than about 1.3.

DETAILED DESCRIPTION OF THE INVENTION

The present invention provides a process for preparing light monoolefins from a feed stream comprising a reactant consisting of methanol, dimethyl ether, or a mixture thereof. The process comprises contacting the feed stream with an aluminosilicate zeolite catalyst having a boron to aluminum atom ratio in the surface region of the catalyst of less than about 1.3. It has been found that the specified amount of boron reduces the formation of coke on the surface region of the catalyst at low exposures and enhances yields of light monoolefins.

As used herein, the expression "light monoolefins" is intended to encompass primarily monoolefins of 2 to 4 carbon atoms, especially ethylene and propylene. The expression "boron to aluminum atom ratio in the surface region of the catalyst" refers to the boron to aluminum ratio determined by Electron Spectroscopy for Chemical Analysis (ESCA). ESCA is a method for analyzing photoejected electrons to determine the presence of atoms on the surface of macromolecules. The method is described in D. M. Hercules, *Anal. Chem.*, 42:20A–40A (1970), the disclosure of which is incorporated herein by reference. In general, photoejected electrons analyzed by this method will come from a surface region on the macromolecule having a depth of less than 10 nm (100 Angstroms) and most of these electrons will come from depths less than 2–5 nm (20–50 Angstroms).

The aluminosilicate zeolite catalyst of the present invention comprises an aluminosilicate zeolite having a silica to alumina ratio of less than about 12. The aluminosilicate zeolite catalyst is prepared by depositing a boron containing species on the surface region of the aluminosilicate zeolite. The aluminosilicate zeolite catalyst has a boron to aluminum atom ratio in the surface region of the catalyst of less than about 1.3. Suitable aluminosilicate zeolites include crystalline and amorphous aluminosilicates. Preferably, the aluminosilicates are crystalline. Most preferably, the aluminosilicate zeolite is a crystalline aluminosilicate selected from the group consisting of chabazite, chabazite-erionite, and erionite. Chabazite-erionite aluminosilicates include, but are not limited to, naturally-occurring chabazites which appear to contain about 60 weight percent chabazite with the remainder being largely erionite. Erionite, and related structures, both natural and synthetic are also most preferred.

Zeolites are generically described as complex aluminosilicates characterized by a three-dimensional framework structure enclosing cavities occupied by ions and water molecules, all of which can move with significant freedom within the zeolite matrix. In commercially useful zeolites, water molecules can be removed from or replaced within the framework without destroying its geometry.

Zeolites can be represented by the following formula:

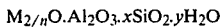

$$M_{2/n}O \cdot Al_2O_3 \cdot xSiO_2 \cdot yH_2O$$

wherein M is a cation of valence n, $x \geq 2$, and y is a number determined by the porosity and the hydration state of the zeolite, generally from 2 to 8. In naturally-occurring zeolites, M is principally represented by Na, Ca, K, Mg, and Ba in proportions usually reflecting their approximate geochemical abundance. The cations M are loosely bound to the structure and can frequently be completely or partially replaced with other cations by conventional ion exchange.

Zeolite structure consists of corner-linked tetrahedra with Al or Si atoms at the centers of tetrahedra and oxygen atoms at corners. Such tetrahedra are combined in a well-defined repeating structure comprising various combinations of 4-, 5-, 6-, 8-, 10-, and 12-membered ring. The resulting framework consists of regular channels and cages which impart a pore structure to the zeolite. Pore dimensions are determined by the geometry of the aluminosilicate tetrahedra forming the zeolite channels and cages.

Useful references generally relating to zeolite structure and characteristics include the following:

W. M. Meier and D. H. Olsen, *Atlas of Zeolite Structure Types* (International Zeolite Assn. 1978);

J. V. Smith, "Origin and Structure of Zeolites" in *Zeolite Chemistry and Catalysis*, J. A. Rabo, ed., Amer. Chem. Soc. Monograph 171 (1976);

R. M. Barrer, "Zeolite Structures" in *Zeolites: Science and Technology*, F. R. Ribeiro et al., ed., NATO ASI Series E-No. 80 (Martinus Nijhoff 1984)

The mineral zeolite chabazite has a structure consisting of identical, near-spherical "chabazite cages", each composed of two 6-rings at top and bottom, six 8-rings in rhombohedral positions, and six pairs of adjacent 4-rings. Each cage, or unit, is thus interconnected to six adjacent units by near-planar, chair-shaped 8-rings. Chabazites can be characterized by the following formula:

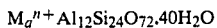

$$M_a{}^{n+}Al_{12}Si_{24}O_{72} \cdot 40H_2O$$

In this formula, the product of a and n is 12. M generally includes Ca, Mg, Na and K.

Erionite exhibits a structure consisting of alternating hexagonal prisms and "cancrinite units". A cancrinite unit is formed by four planar 6-rings, each of which shares two edges with adjacent 6-rings, joined by three pairs of adjacent 4-rings. The hexagonal prisms and cancrinite units of erionite are crosslinked by 4-rings and single 6-rings to form a complex system of channels interconnected by 8-rings. Erionite can be characterized by the following formula:

$$(Na_2,Ca)_{4.5}Al_9Si_{27}O_{72}.27H_2O$$

The catalytic activity of suitable zeolite minerals can be significantly improved by replacing the major portion of naturally-occurring alkali or alkaline earth metals with hydrogen ions. The alkali or alkaline earth metal ions can be exchanged or protons in a conventional ion exchange with $H^+$ or by conversion to an ammoniated form (e.g., $NH_4^+$-chabazite) which is subsequently converted to the $H^+$ or acid form by calcination at elevated temperatures. Generally, calcination temperatures of from 400° C. to about 600° C. are satisfactory. Procedures for carrying out the hydrogen-exchange are well known and are included in U.S. Pat. Nos. 4,062,905; 4,075,095; and 4,075,096.

Zeolites which are suitable for use in the process of this invention may also contain cations of various metals, such as those of strontium and barium. Metal cations are introduced into zeolite structures by ion-exchange methods known in the art, like cation exchange of the zeolite in its hydrogen form. Suitable zeolites can have large or small pores provided that the molar silica to alumina ratio is less than 12.

The aluminosilicate catalyst of the present invention is prepared by depositing a specified amount of a boron containing species on the surface region of a suitable aluminosilicate zeolite. The sources of suitable boron containing species are boron compounds which can be in the liquid phase in the form of a pure liquid or as a solute in a liquid solution. The boron compound can also be in the gas phase in the form of a pure gas or mixed with an inert gas such as argon or nitrogen. Suitable boron compounds for generating the boron containing species include trimethyl-, triethyl-, tri-n-propyl, and tri-n-butylborate. Other boron compounds such as borate esters, boron halides, boranes, borates, alkyl borates, and borazenes are also suitable. Preferably, the boron compound is a borate. Although not always necessary, calcination can be carried out by heating the treated zeolite at a temperature lower than the zeolite decomposition temperature but high enough to convert the boron source compound to boron oxide.

The amount of boron to be deposited on the zeolite must be sufficient to be effective but not so much as to eliminate the catalytically active internal sites. It has been found that boron should be deposited in an amount such that the boron to aluminum atom ratio of the surface region, as determined by ESCA, is less than about 1.3. Even small amounts of boron as detected by ESCA result in improvement in yield of the desired monoolefins. It has been found that deposition of boron in an amount such that the boron to aluminum atom ratio in the surface region of the catalyst, as determined by ESCA, is greater than about 1.3 deactivates the catalyst.

In the process of the present invention, light monoolefins are prepared by contacting a boron-treated aluminosilicate zeolite catalyst with a feed stream comprising a reactant consisting of methanol, dimethyl ether, or mixtures thereof. Reaction conditions include an operating temperature of from about 350° to about 600° C.; a pressure of from about 20 to about 3000 kPa (about 0.2 to about 30 atm), preferably from about 100 to about 1500 kPa; and a weight hourly space velocity of greater than about 0.5 $h^{-1}$, preferably from about 1 to about 150 $h^{-1}$. Weight hourly space velocity is defined as the grams of feed stream fed per hour divided by the grams of catalyst.

Suitable feed streams comprise a reactant consisting of methanol, dimethyl ether, or mixtures thereof. Other materials may be present in the feed stream; provided that, such materials do not substantially adversely affect the yield of desired monoolefins. Water is not required in the present process. However, when the feed stream consists of dimethyl ether, it is preferable to have sufficient water in the feed stream such that the water to dimethyl ether mole ratio is at least about 0.3. Methanol contained in a feed stream is converted to dimethyl ether and water under reaction conditions. More specifically, one mole of methanol is converted to 0.5 mole of dimethyl ether and 0.5 mole of water. Additional water is not required to achieve a preferred water to dimethyl ether atom ratio when sufficient methanol is present in the feed stream.

In the process of the present invention, at least about 85 weight percent of the reactant is converted to hydrocarbons comprising at least 60 weight percent ethylene and propylene. The 85 weight percent conversion is achieved before the contacting has exceeded 0.3 gram of reactant per gram of catalyst, preferably before exceeding 0.1 gram of reactant per gram of catalyst.

The process can be carried in a continuous or a semi-continuous mode of operation. In one preferred embodiment, a pre-mixed charge of reactant and water is passed in vapor form through a fixed bed of granulated catalyst maintained at the reaction temperature. Alternatively, the catalyst particles can be moving, for example, fluidized, and the feed gas stream passed concurrently or countercurrently through the catalyst. The process of the invention could also be carried out in a cyclic mode wherein in each cycle the catalyst is exposed to the feed gas stream for a suitable reaction period, for example, 1 to 20 minutes, and then is exposed to air or to a mixture of steam and air for a suitable regeneration period, for example, 30 to 60 minutes. Continuous uninterrupted conversion of reactants to hydrocarbons can be achieved by operating two or more such beds in parallel with one or more beds in the reaction mode at any given time and the other(s) in the regenerator mode.

The present invention is further described by the following examples, wherein all parts and percentages are by weight and degrees are Celsius. As used in the Examples, weight hourly space velocity (WHSV) is defined as the grams of feed fed per hour divided by the grams of catalyst. The ratio of the total amount of dimethyl ether (DME) passed over the catalyst to the amount of catalyst present (g DME/g catalyst) increased with the length of period of time that the feed gas stream is fed to the catalyst, i.e. with the contact time. The contact time is defined as the ratio of gaseous volume flow rate to the volume of the catalyst. The conversion of reactant is based on the amount of reactant carbon which is converted to hydrocarbons.

EXAMPLE 1

Triethylborate-treated Zeolite Sr-Erionite

A triethylborate-treated zeolite catalyst was prepared according to the following procedure. An aqueous solution was prepared containing 10% Sr(NO$_3$)$_2$. 20 g of a zeolite NH$_4$+-erionite, available commercially from the Linde Company under the tradename Linde E-10 (Lot Number 4969-92), were ion exchanged with a 200 mL portion of the solution at 90° for one hour. The zeolite was filtered and the exchange procedure was repeated two additional times. The resulting zeolite was washed thoroughly with water and dried at 110°. 9 g of the resulting dried material were stirred for three hours in 25 mL of triethylborate (B(OEt)$_3$). The resulting slurry was filtered and the resulting filtrate was dried in flowing air. The dried filtrate was treated with a programmed air calcination in a muffle furnace. The temperature of the furnace was increased from ambient temperature to 540° at a rate of 50°/hour. The filtrate was then heated at 540° for ten hours, to form a catalyst powder. ESCA measurements on the catalyst powder showed a surface boron to aluminum atom ratio of 0.45.

The catalyst powder was made into a wafer having a thickness of ⅛ in (0.3 cm) in a hydraulic press at 6,000 psia (41,000 kPa). The resulting wafer was crushed to form catalyst particles which were separated into fractions based on size. 2.0 mL (approximately 1 g) of catalyst particles which were capable of being sieved in sieves having 850 μm to 425 μm openings (No. 20 to No. 40 U.S. Standard Sieve), were placed in a U-tube reactor immersed in a fluidized, heated sand bed. The catalyst particles were heated to a desired reaction temperature of 450° under steam. Water and dimethyl ether were fed into the reactor at flow rates of 5.0 g/hour and 3.6 g/hour, respectively. By means of a mixing tee, the dimethyl ether was admixed with the water to form a feed stream having a mole ratio of water to dimethyl ether of 78/22. The feed stream was fed into the reactor for periods of time ranging from 5 to 30 minutes as indicated in Table I. Contact times were 0.32 seconds and the feed stream had a weight hourly space velocity of 8.6 h$^{-1}$. At the end of each time period, exit gases were analyzed by gas chromatography. The results are shown in Table I.

EXAMPLE 2

Boron Trichloride-treated Zeolite Chabazite-Erionite 10.4 g of a zeolite H+-chabazite-erionite, available commercially for the Norton Company under the registered trademark Zeolon 500H+, were dehydrated in a quartz tube in a vertically mounted tube furnace at 500° for 2.5 hours under a stream of Ar. The zeolite was cooled to 100°. A stream of a 20% BCl$_3$/Ar mixture in air was passed through the zeolite as the temperature of the furnace was raised to 200° at a rate of 10°/minute and then to 300° at a rate of 20°/minute. The temperature was held at 300° for 1.25 hours and the BCl$_3$/Ar stream was then converted to only Ar. The temperature of the furnace was maintained at 300° for one more hour and then lowered to ambient temperature. The resulting catalyst powder was washed with distilled water to lower the chloride content and dried at 110°. ESCA measurements on the catalyst powder showed a surface boron to aluminum atom ratio of less than 0.011.

Catalyst particles were prepared from the catalyst powder according to the method described in Example 1. Dimethyl ether was passed over the resulting catalyst particles according to the method described in Example 1, except that the reaction temperature was 460°. The results are shown in Table II.

TABLE II

| Reaction Time (min) | Reactant Contacted g DME / g catalyst | Feed Gas H$_2$O mole % | Conversion (wt %) | Hydrocarbon Selectivity (wt %) | | | | | | |
|---|---|---|---|---|---|---|---|---|---|---|
| | | | | CH$_4$ | C$_2$H$_4$ | C$_2$H$_6$ | C$_3$H$_6$ | C$_3$H$_8$ | C$_4$+ | C$_2$H$_4$ + C$_3$H$_6$ |
| 5 | 0.30 | 78 | 100 | 4 | 34 | 3 | 32 | 15 | 11 | 66 |
| 10 | 0.60 | 78 | 100 | 5 | 40 | 2 | 34 | 9 | 10 | 74 |
| 15 | 0.90 | 78 | 100 | 5 | 49 | 2 | 33 | 5 | 7 | 82 |
| 20 | 1.20 | 78 | 100 | 6 | 53 | 1 | 32 | 2 | 6 | 85 |
| 25 | 1.50 | 78 | 76 | 7 | 57 | 1 | 30 | 1 | 4 | 87 |
| 30 | 1.80 | 78 | 54 | 6 | 60 | 1 | 28 | 2 | 3 | 88 |

EXAMPLE 3

Triethylborate-treated Zeolite NH$_4$+-Erionite 25 g of a zeolite NH$_4$+-erionite, similar to that of Example 1, were placed in 60 mL of triethylborate for three hours. The resulting slurry was filtered and dried at 110°. The resulting filtrate was treated with a programmed air calcination, as described in Example 1, to form a catalyst powder. ESCA measurements on the catalyst powder showed a surface boron to aluminum atom ratio of 0.041.

Catalyst particles were prepared from the catalyst powder according to the method described in Example 1. Dimethyl ether was passed over the resulting catalyst particles according to the method described in Example 1, except that the reaction periods ranged from 10 to 30 minutes. The results are shown in Table III.

TABLE I

| Reaction Time (min) | Reactant Contacted g DME / g catalyst | Feed Gas H$_2$O mole % | Conversion (wt %) | Hydrocarbon Selectivity (wt %) | | | | | | |
|---|---|---|---|---|---|---|---|---|---|---|
| | | | | CH$_4$ | C$_2$H$_4$ | C$_2$H$_6$ | C$_3$H$_6$ | C$_3$H$_8$ | C$_4$+ | C$_2$H$_4$ + C$_3$H$_6$ |
| 5 | 0.30 | 78 | 100 | 3 | 51 | 1 | 30 | <1 | 12 | 81 |
| 10 | 0.60 | 78 | 100 | 5 | 54 | 1 | 28 | <1 | 11 | 82 |
| 15 | 0.90 | 78 | 100 | 5 | 56 | 1 | 27 | <1 | 10 | 83 |
| 20 | 1.20 | 78 | 87 | 5 | 60 | 1 | 25 | <1 | 8 | 85 |
| 25 | 1.50 | 78 | 71 | 6 | 60 | 1 | 24 | <1 | 8 | 84 |
| 30 | 1.80 | 78 | 64 | 6 | 60 | 1 | 24 | <1 | 8 | 84 |

TABLE III

| Reaction Time (min) | Reactant Contacted g DME / g catalyst | Feed Gas H$_2$O mole % | Conversion (wt %) | Hydrocarbon Selectivity (wt %) | | | | | | |
|---|---|---|---|---|---|---|---|---|---|---|
| | | | | CH$_4$ | C$_2$H$_4$ | C$_2$H$_6$ | C$_3$H$_6$ | C$_3$H$_8$ | C$_4$$^+$ | C$_2$H$_4$ + C$_3$H$_6$ |
| 10 | 0.60 | 78 | 100 | 5 | 47 | 2 | 32 | <1 | 11 | 79 |
| 16 | 0.96 | 78 | 100 | 6 | 57 | 2 | 25 | <1 | 14 | 82 |
| 25 | 1.50 | 78 | 48 | 9 | 62 | 2 | 21 | <1 | 5 | 83 |
| 30 | 1.80 | 78 | 14 | 14 | 60 | 2 | 17 | <1 | 6 | 77 |

EXAMPLE 4

Triethylborate-treated Zeolite NH$_4$$^+$-Erionite

The triethylborate-treated zeolite catalyst particles prepared in Example 3 were used in this Example. Dimethyl ether was passed over the catalyst particles, according to the method described in Example 1, except that the water flow rate was 1.45 g/hour, the dimethyl ether flow rate was 5.9 g/hour, the mole ratio of water to dimethyl ether was 31/69, the weight hourly space velocity was 7.35 h$^{-1}$, and the reaction periods ranged from 5 to 15 minutes. The results are shown in Table IV.

TABLE IV

| Reaction Time (min) | Reactant Contacted g DME / g catalyst | Feed Gas H$_2$O mole % | Conversion (wt %) | Hydrocarbon Selectivity (wt %) | | | | | | |
|---|---|---|---|---|---|---|---|---|---|---|
| | | | | CH$_4$ | C$_2$H$_4$ | C$_2$H$_6$ | C$_3$H$_6$ | C$_3$H$_8$ | C$_4$$^+$ | C$_2$H$_4$ + C$_3$H$_6$ |
| 5 | 0.30 | 31 | 100 | 5 | 44 | 2 | 33 | <1 | 15 | 77 |
| 10 | 0.59 | 31 | 79 | 6 | 57 | 1 | 25 | <1 | 10 | 82 |
| 13 | 0.77 | 31 | 45 | 7 | 58 | 1 | 23 | <1 | 9 | 81 |
| 15 | 0.89 | 31 | 40 | 8 | 58 | 1 | 21 | <1 | 9 | 79 |

EXAMPLE 5

Triethylborate-treated Zeolite NH$_4$$^+$-Erionite

The triethylborate-treated zeolite catalyst particles prepared in Example 3 were used in this Example. Dimethyl ether was passed over the catalyst particles, according to the method described in Example 1, except that the water flow rate was 0.36 g/hour, the dimethyl ether flow rate was 6.64 g/hour, the mole ratio of water to diemthyl ether was 7.8/92.2, the weight hours space velocity was 7.0 h$^{-1}$, and the reaction periods were 5 and 10 minutes. The results are shown in Table V.

TABLE V

| Reaction Time (min) | Reactant Contacted g DME / g catalyst | Feed Gas H$_2$O mole % | Conversion (wt %) | Hydrocarbon Selectivity (wt %) | | | | | | |
|---|---|---|---|---|---|---|---|---|---|---|
| | | | | CH$_4$ | C$_2$H$_4$ | C$_2$H$_6$ | C$_3$H$_6$ | C$_3$H$_8$ | C$_4$$^+$ | C$_2$H$_4$ + C$_3$H$_6$ |
| 5 | 0.33 | 7.8 | 100 | 7 | 45 | 2 | 29 | <1 | 14 | 74 |
| 10 | 0.66 | 7.8 | 27 | 12 | 54 | 2 | 23 | <1 | 8 | 77 |

Examples 3, 4 and 5 show that, although the water content of the feed stream varied from 78 mole percent to 7.8 mole percent, the selectivity to ethylene and propylene showed little change. Thus, the reaction is not significantly affected by the amount of water present in the feed stream.

EXAMPLE 6

Pre-equilibrated Triethylborate-treated Zeolite NH$_4$$^+$-Erionite 25 g of a zeolite NH$_4$$^+$-erionite, similar to that of Example 1, were placed over a saturated NH$_4$Cl solution for 24 hours. The resulting "equilibrated" zeolite was stirred in 60 mL of triethylborate for three hours. The resulting slurry was filtered and the resulting filtrate was dried in flowing air. The filtrate was treated with the programmed air calcination, described in Example 1, to form a catalyst powder. ESCA measurements on the catalyst powder showed a surface boron to aluminum atom ratio of 0.146.

Catalyst particles were prepared from the catalyst powder according to the method described in Example 1. Dimethyl ether was passed over the resulting catalyst particles according to the method described in Example 1, except that the reaction periods ranged from 1 to 17 minutes. The results are shown in Table VI.

TABLE VI

| Reaction Time (min) | Reactant Contacted g DME / g catalyst | Feed Gas H$_2$O mole % | Conversion (wt %) | Hydrocarbon Selectivity (wt %) | | | | | | |
|---|---|---|---|---|---|---|---|---|---|---|
| | | | | CH$_4$ | C$_2$H$_4$ | C$_2$H$_6$ | C$_3$H$_6$ | C$_3$H$_8$ | C$_4$$^+$ | C$_2$H$_4$ + C$_3$H$_6$ |
| 1 | 0.06 | 78 | 100 | 6 | 40 | 2 | 26 | 11 | 16 | 66 |
| 2 | 0.12 | 78 | 100 | 7 | 43 | 1 | 31 | 10 | 6 | 74 |
| 3 | 0.18 | 78 | 100 | 5 | 40 | 1 | 27 | 7 | 18 | 67 |
| 5 | 0.30 | 78 | 100 | 4 | 41 | 2 | 26 | 8 | 18 | 67 |
| 12 | 0.72 | 78 | 74 | 3 | 48 | 1 | 23 | 5 | 18 | 71 |
| 17 | 1.02 | 78 | 25 | 3 | 50 | 1 | 22 | 4 | 18 | 72 |

EXAMPLE 7

Triethylborate-treated Zeolite Sr-Erionite

A triethylborate-treated zeolite catalyst was prepared according to the following procedure. An aqueous solution was prepared containing 10% $Sr(NO_3)_2$. 30 g of the zeolite $NH_4^+$-erionite described in Example 1 was ion exchanged with a 300 mL portion of the solution at 90° for one hour. The zeolite was filtered and the exchange procedure was repeated two additional times. The resulting zeolite was washed thoroughly with water and dried at 110°. 30 g of the resulting dried material was stirred for three hours in 65 mL of triethylborate (B(O-Et)$_3$). The resulting slurry was filtered and the resulting filtrate was dried in flowing air. The dried filtrate was treated with the programmed air calcination, described in Example 1, to form a catalyst powder. ESCA measurements on the catalyst showed a surface boron to aluminum atom ratio of 1.21.

Catalyst particles were prepared from the catalyst powder according to the method described in Example 1. Dimethyl ether was passed over the resulting catalyst particles according to the method described in Example 1, except that instead of water being fed at a flow rate of 5 g/hour, nitrogen was fed at a flow rate of 100 mL/minute. The results are shown in Table VII.

TABLE VII

| Reaction Time (min) | Reactant Contacted g DME / g catalyst | Feed Gas $H_2O$ mole % | Conversion (wt %) | Hydrocarbon Selectivity (wt %) | | | | | | |
|---|---|---|---|---|---|---|---|---|---|---|
| | | | | $CH_4$ | $C_2H_4$ | $C_2H_6$ | $C_3H_6$ | $C_3H_8$ | $C_4^+$ | $C_2H_4 + C_3H_6$ |
| 1 | .06 | 0 | 100 | 5 | 25 | 1 | 34 | 9 | 15 | 59 |
| 2 | .12 | 0 | 100 | 4.2 | 25 | 1 | 32 | 7 | 16 | 57 |
| 3 | .18 | 0 | 100 | 4.4 | 26 | 1 | 34 | 6 | 16 | 60 |
| 5 | .30 | 0 | 100 | 4.8 | 29 | 1 | 31 | 5 | 15 | 60 |
| 8 | .48 | 0 | 100 | 5.0 | 31 | 1 | 31 | 4 | 15 | 62 |
| 12 | .72 | 0 | 86 | 5.1 | 36 | 1 | 29 | 3 | 15 | 65 |

COMPARATIVE EXPERIMENT A

Zeolite $NH_4^+$-Erionite-No Boron Treatment

A zeolite catalyst with no boron treatment was prepared according to the following procedure. 50 g of the zeolite $NH_4^+$-erionite, described in Example 1, were calcined at 500° under flowing $N_2$ for ten hours. An aqueous solution was prepared containing 10% $NH_4NO_3$. The calcined zeolite was ion exchanged with a 500 mL portion of the solution at 90° for 1 hour. The zeolite was filtered and the exchange procedure was repeated two additional times. The resulting zeolite was washed thoroughly with water and dried at 110°. The resulting dried material was treated with a programmed air calcination according to the method described in Example 1, to form a catalyst powder.

Catalyst particles were prepared from the catalyst powder according to the method described in Example 1. Dimethyl ether was passed over the resulting catalyst particles according to the method described in Example 1 except that the reaction periods ranged from 5 to 20 minutes. The results are shown in Table VIII.

TABLE VIII

| Reaction Time (min) | g DME / g catalyst | Conversion (wt %) | Hydrocarbon Selectivity (wt %) | | | | | | |
|---|---|---|---|---|---|---|---|---|---|
| | | | $CH_4$ | $C_2H_4$ | $C_2H_6$ | $C_3H_6$ | $C_3H_8$ | $C_4^+$ | $C_2H_4 + C_3H_6$ |
| 5 | 0.30 | 100 | 3 | 30 | 3 | 24 | 19 | 18 | 54 |
| 10 | 0.60 | 100 | 5 | 37 | 3 | 36 | <1 | 16 | 73 |
| 15 | 0.90 | 100 | 4 | 43 | 3 | 34 | <1 | 15 | 77 |
| 20 | 1.20 | 82 | 4 | 47 | 2 | 32 | <1 | 13 | 79 |

A comparison of these results with those of Examples 3, 4 and 5 in which the catalyst used was prepared from the same zeolite $NH_4^+$-erionite show that boron treated catalysts achieve higher yields of ethylene and propylene at shorter contact times and at reduced water to dimethyl ether molar ratios than non-treated catalysts.

COMPARATIVE EXPERIMENT B

Zeolite $NH_4^+$-Erionite-No Boron Treatment 20 g of the zeolite $NH_4^+$-erionite, described in Example 1, were treated with a programmed air calcination in a muffle furnace. The temperature of the furnace was increased from ambient temperature to 540° at a rate of 50°/hour and then held at 540° for 10 hours, to form a catalyst powder.

Catalyst particles were prepared from the catalyst powder according to the method described in Example 1. Dimethyl ether was passed over the resulting catalyst particles according to the method described in Example 1 except the reaction periods ranged from 5 to 25 minutes. The results are shown in Table IX.

TABLE IX

| Reaction Time (min) | g DME / g catalyst | Conversion (wt %) | Hydrocarbon Selectivity (wt %) | | | | | | |
|---|---|---|---|---|---|---|---|---|---|
| | | | $CH_4$ | $C_2H_4$ | $C_2H_6$ | $C_3H_6$ | $C_3H_8$ | $C_4^+$ | $C_2H_4 + C_3H_6$ |
| 5 | 0.30 | 100 | 21 | 36 | 3 | 14 | <1 | 26 | 50 |
| 10 | 0.60 | 100 | 29 | 43 | 3 | 18 | <1 | 5 | 61 |
| 15 | 0.90 | 100 | 36 | 46 | 3 | 11 | <1 | 4 | 57 |
| 25 | 1.50 | 30 | 46 | 40 | 2 | 8 | <1 | 4 | 48 |

A comparison of these results with those of Examples 3, 4 and 5 in which the catalyst used was prepared from the same zeolite $NH_4^+$-erionite show that boron treated catalysts achieve higher yields of ethylene and propylene at shorter contact times and at reduced water to dimethyl ether molar ratios than non-treated catalysts.

COMPARATIVE EXPERIMENT C

Equilibrated Triethylborate-twice-treated Zeolite $NH_4^+$-Erionite

About 12 g of the pre-equilibrated triethylborate-treated zeolite $NH_4^+$-erionite prepared in Example 6 was again placed over a saturated $NH_4Cl$ solution for 24 hours. The resulting equilibrated zeolite was stirred in 35 mL of triethylborate for 3 hours. The resulting slurry was filtered, and the resulting filtrate was dried in flowing air. The dried filtration was treated with a programmed air calcination, according to the method described in Example 1, to form a catalyst powder. ESCA measurements on the catalyst powder showed a surface boron to aluminum atom ratio of 1.71.

Catalyst particles were prepared from the catalyst powder according to the method of Example 1. Dimethyl ether was passed over the resulting catalyst particles according to the method of Example 1 except that the reaction periods ranged from 2 to 10 minutes. The results are shown in Table X.

TABLE X

| Reaction Time (min) | g DME / g catalyst | Conversion (wt %) | Hydrocarbon Selectivity (wt %) | | | | | | |
|---|---|---|---|---|---|---|---|---|---|
| | | | $CH_4$ | $C_2H_4$ | $C_2H_6$ | $C_3H_6$ | $C_3H_8$ | $C_4^+$ | $C_2H_4 + C_3H_6$ |
| 2 | 0.12 | 22 | 14 | 45 | 4 | 18 | <1 | 15 | 63 |
| 5 | 0.30 | 16 | 10 | 51 | 3 | 24 | <1 | 10 | 75 |
| 10 | 0.60 | 7 | 8 | 61 | 3 | 18 | <1 | 10 | 79 |

A comparison of these results with those of Example 6 show that the additional boron deposited onto the catalyst of this Comparative Experiment resulted in a lower converion of dimethyl ethers.

What is claimed is:

1. A process for preparing light monoolefins from a feed stream comprising a reactant consisting of methanol, dimethyl ether, or a mixture thereof, comprising contacting the feed stream at a weight hourly space velocity of greater than about 0.5 $h^{-1}$ with an aluminosilicate zeolite catalyst at a temperature of from about 350° to about 600° C. and a pressure of from about 20 to about 3000 kPa to convert at least about 85 weight percent of the reactant to hydrocarbons comprising at least 60 weight percent ethylene and propylene, said 85 weight percent conversion being achieved before the contacting has exceeded 0.3 gram of reactant per gram of catalyst;

said aluminosilicate zeolite catalyst comprising an aluminosilicate zeolite having a silica to alumina ratio of less than about 12; said aluminosilicate zeolite catalyst being prepared by depositing a boron containing species on the surface region of the aluminosilicate zeolite; said aluminosilicate zeolite catalyst having a boron to aluminum atom ratio in the surface region of the catalyst of less than about 1.3.

2. A process as defined in claim 1, wherein said 85 weight percent conversion is achieved before the contacting has exceeded 0.1 gram of reactant per gram of catalyst.

3. A process as defined in claim 1, wherein the aluminosilicate zeolite a crystalline aluminosilicate is selected from the group consisting of chabazite, chabazite-erionite and erionite.

4. A process as defined in claim 3, wherein the boron containing species is generated from a boron compound selected from the group consisting of borate esters, boron halides, boranes, borates, alkyl borates, and borazenes.

5. A process as defined in claim 4, wherein the boron compound is a borate.

6. A process as defined in claim 5, wherein the temperature is from about 450° to about 520° C.

7. A process as defined in claim 6, wherein the weight hourly space velocity is from about 1 to about 150 $h^{-1}$.

* * * * *